United States Patent [19]
Achter et al.

[11] Patent Number: 5,510,620
[45] Date of Patent: Apr. 23, 1996

[54] DETECTION OF TURBID OR FOAMING CONTAMINANTS IN CONTAINERS

[75] Inventors: Eugene K. Achter; David Lieb, both of Lexington; John S. Beaty, Belmont; Helmut W. Klotzsch, Groton; Craig D. Thompson, Natick; Jonathan Bosworth, Acton, all of Mass.

[73] Assignee: Thermedics Detection, Inc., Waltham, Mass.

[21] Appl. No.: 268,198

[22] Filed: Jun. 29, 1994

Related U.S. Application Data

[63] Continuation-in-part of Ser. No. 198,217, Feb. 17, 1994.

[51] Int. Cl.$^6$ ............................................. G01N 21/90
[52] U.S. Cl. ............................ 250/339.12; 356/337
[58] Field of Search ................... 250/339.12, 339.06, 250/339.09, 339.07; 356/409, 413, 436, 337

[56] References Cited

U.S. PATENT DOCUMENTS

| | | | |
|---|---|---|---|
| 4,221,961 | 9/1980 | Peyton | 250/223 B |
| 4,459,023 | 7/1984 | Reich et al. | 356/237 |
| 4,490,042 | 12/1984 | Wyatt | 356/340 |
| 4,551,627 | 11/1985 | Reich | 250/339 |
| 4,830,192 | 5/1989 | Plester et al. | 209/3.1 |
| 4,858,768 | 8/1989 | Plester | 209/3.1 |
| 4,998,824 | 3/1991 | Littlejohn et al. | 356/407 |
| 5,002,397 | 3/1991 | Ingrum et al. | 356/407 |
| 5,067,616 | 11/1991 | Plester et al. | 209/3.1 |

*Primary Examiner*—Davis L. Willis
*Assistant Examiner*—Richard Hanig
*Attorney, Agent, or Firm*—Fish & Richardson

[57] ABSTRACT

To detect a contaminant in a moving container, radiant energy is directed into the moving container. Thereafter, a level of radiant energy scattered by contents of the moving container is detected. The presence of a contaminant is indicated when the detected level of scattered radiant energy differs from a threshold level. Scattered radiant energy detected by the system includes that scattered by turbid materials within the container and that scattered by foam within the container. Detection of turbid materials or foam may be combined with spectral contaminant detection.

27 Claims, 6 Drawing Sheets

DETECTION OF TURBID OR FOAMING CONTAMINANTS IN CONTAINERS

CROSS-REFERENCE TO RELATED APPLICATIONS

This application is a continuation-in-part of co-pending U.S. patent application Ser. No. 08/198,217, which is entitled "SPECTRAL DETECTION OF CONTAMINANTS IN CONTAINERS" and was filed on Feb. 17, 1994.

BACKGROUND OF THE INVENTION

The invention relates to detection of contaminants in containers, particularly contaminants whose presence is manifested by turbidity of a liquid or foam on top of the liquid.

The popularity of refillable containers has increased as the costs, both social and financial, associated with disposal of packaging have become less acceptable. For example, in many countries, water and other beverages are sold in refillable bottles. These bottles are often made from a type of plastic known as polyethylene terephthalate.

After use, refillable containers are returned to a bottling plant where they are cleaned and inspected before being refilled. This inspection, in addition to checking for physical damage such as cracks, screens the containers to eliminate those that include contaminants that might degrade the flavor, safety, or other qualities of the product that they contain. The risk of contamination is greater when a container is made from plastic, as opposed to glass, because some contaminants can be absorbed into the plastic walls of the container. Absorbed contaminants can persist despite cleaning procedures, and can later leach into the product.

Though some contaminants, such as detergents and fabric softeners, are visibly colored and can be detected by human inspectors, such human visual inspection is undesirable when bottles or other containers are moving on high speed conveyors and stopping or touching the bottles to perform an inspection is undesirable or overly expensive. Moreover, such human visual inspection is subject to lapses in attention by the inspectors.

As an alternative, it has been suggested to use spectrophotometric instrumentation to automatically detect colored contaminants. Spectrophotometric instrumentation for color detection is well known in many fields, including laboratory analysis of chemical solutions, and quality control functions in the paint, fabric, and photographic industries. In general, spectrophotometric analysis of liquid samples is based on Beer's Law, which states that the optical density (i.e., the log ratio of transmitted or detected light intensity to incident light intensity) is directly proportional to the concentration of the chemical compound giving rise to the absorption of light. Beer's law is discussed, for example, in H. A. Strobel, *Chemical Instrumentation*, pp. 148–53 (1960, Addison Wesley, Reading, Mass.). Beer's law is limited in that it can only be applied if all of the detected light travels the same distance through the absorbing medium. In chemical spectrophotometric analysis, this is done by placing the liquid sample in a cuvette, or optical cell, having parallel windows that are typically spaced apart by ten millimeters.

When a container is mostly filled with liquid, a narrow optical beam can be directed radially through the container so that it intersects the major vertical axis of the container in a region where the wall of the container is substantially parallel to the major vertical axis. In the case of a cylindrical container such as a bottle, if the beam is very narrow relative to diameter of the bottle, all of the detected light travels over substantially the same path length through the bottle, and the geometrical conditions for Beer's law are satisfied.

However, when a bottle or other container only contains a few millimeters of residual liquid, it becomes much more difficult to utilize Beer's law. For example, in refillable plastic beverage bottles, the walls of the bottle curve inward near the bottom of the bottle and are not parallel to the major axis of the bottle. Also, many refillable plastic bottles include a dome in the bottom of the bottle. In these situations, refraction and reflection result in the detected light travelling over a variety of path lengths, and Beer's law cannot be applied.

One way of dealing with these difficulties is to mechanically tilt the bottle to pool the residual liquid in a corner of the bottle and arrange the incident beam of light perpendicular to the face of the bottle to minimize refractive effects. In this case, as long as the beam of light is sufficiently thin and the dome avoided, the path length will be well defined and free of multiple reflections, and conventional Beer's law analysis can be applied. However, mechanical arrangements to provide such tilting may be complex and difficult to integrate with a high speed conveyor utilized in the processing of refillable containers.

SUMMARY OF THE INVENTION

The invention features detection of contaminants such as detergents in moving containers by measuring light scattered by particles in turbid liquid which may be near the bottom of the container, or by foam at the top of the liquid. Radiant energy such as a laser beam is directed into an opening at the top of the container. If liquid in the container is turbid, the radiant energy is scattered by the liquid. To a human observer, this scattered radiant energy appears as a column of light in the liquid. Foam in the container also scatters the radiant energy. According to the invention, scattered radiant energy encounters appropriately positioned detectors so that contaminants such as detergents are detected by monitoring the level of energy incident on the detectors and indicating the presence of a contaminant when this level differs from a threshold level. When contaminants are detected, the container is rejected.

In one aspect, generally, the invention features detecting contaminants in a moving container by directing radiant energy into the moving container, detecting a level of radiant energy scattered by contents of the moving container, and indicating the presence of a contaminant when the detected level of scattered radiant energy differs from a threshold level. Scattered radiant energy can include that scattered by turbid liquid within the container, foam within the container, or both.

Scattered radiant energy can be detected in a number of ways. In one approach, energy scattered in a different direction than that at which the radiant energy is directed into the container is measured and the presence of a contaminant is indicated when the energy incident on the detector exceeds a threshold. In another approach, energy passing through the container in the direction at which the energy enters the container is measured. In this case, because the transmitted energy is inversely related to the scattered energy, the presence of a contaminant is indicated when the energy incident on the detector is less than a threshold. In either case, to reduce the effects of background energy, the radiant energy is modulated before it is directed into the moving container and demodulated after detection.

The invention also features examining the color of the container and any contents thereof and, based on this examination, either adjusting the threshold for detection of scattered energy, spectrally detecting contaminants, or both. Thus, according to the invention, colored contaminants in a container are detected without requiring the mechanical complexity associated with tilting and orienting the bottle at high speeds even when the container includes only a minimal amount of liquid.

To spectrally detect contaminants in a moving container, liquid is added to the container to ensure the presence of a minimal amount needed for proper detection. Spectral characteristics of the liquid are determined by subjecting the container and the liquid to wideband radiant energy and obtaining a resulting spectrum. This spectrum, without consideration of the intensity of the radiant energy directed at the container, is then compared against a library of stored reference spectra to determine whether contaminants are present. If contaminants are determined to be present, the container is rejected. The results of the comparison can also be used to adjust the thresholds for turbid contaminant and/or foam detection. In general, the radiant energy used to detect turbid contaminants or foam is concentrated in a narrow band of wavelengths while the radiant energy used to generate frequency spectra covers a much wider band of wavelengths. (The expression "turbid contaminant" is used herein to refer to a contaminant whose presence in a liquid results in the liquid being turbid or unclear so as to scatter radiant energy that is directed into the liquid.)

For improved performance, two spectra are obtained for each container, and each is compared to corresponding reference spectra. The spectra are obtained, for example, by measuring a first spectrum when a container is located in a first position, moving the container to a second position, and measuring a second spectrum. In this approach, the two spectra can be obtained using only a single source of radiant energy and a single detector.

Typically, the source of wideband radiant energy and the detector are angled relative to each other (i.e., the source of wideband radiant energy and the detector are not coaxial), and are positioned so that the radiant energy that passes from the source to the detector passes through a region substantially near the bottom of the container. The preferred range for this angle is from 100° to 140° with the most preferred angle being at about 120°.

The amount of liquid and the concentration of contaminants in a container can vary to a large degree. Thus, to avoid falsely rejecting uncontaminated containers, features of the spectra that are relatively unaffected by variations in liquid level or concentration are employed.

The spectra employed in spectral detection are preferably an "absorption" spectrum, which provides a measurement of the radiation absorbed by the liquid and any contaminants therein, and a "reflection" spectrum, which provides a measurement of the radiation reflected by the liquid and any contaminants therein. While the absorption spectrum and the reflection spectrum each provide accurate contaminant detection, improved accuracy of detection is achieved through use of both spectra.

The library of reference spectra against which the measured spectra are compared can include spectra associated with only uncontaminated containers, only contaminated containers, or both contaminated and uncontaminated containers. When the library includes spectra for only uncontaminated containers, the presence of a contaminant is indicated when the spectra of the container differs from all of the spectra in the library by a predetermined threshold. When the library includes spectra for only contaminated containers, the presence of a contaminant is indicated when the spectra of the container matches, within a predetermined threshold, a spectrum from the library. Finally, when the library includes spectra for both contaminated and uncontaminated containers, the presence of a contaminant is indicated when the spectra of the container differs from each of the reference spectra associated with an uncontaminated container by more than a predetermined threshold or matches, within a predetermined threshold, a reference spectrum associated with a contaminated container.

Generally, only a small amount of liquid is added to a container prior to directing radiant energy into the container. In some applications, this amount is less than ten milliliters. Often, only four and a half milliliters are used. The liquid is added at high pressure to agitate any contaminants within the container, and is typically added in multiple bursts for the same reason. Water or a dilute aqueous solution is generally the liquid added.

Various forms of radiant energy can be used in generating the spectra. In certain applications, either visible light, infrared energy, or a combination of the two are preferred.

The invention is particularly useful for detecting contaminants in clear plastic bottles, such as those made from polyethylene terephthalate. However, the invention is also useful in detecting contaminants within other types of containers, containers made from other materials, and tinted containers. Generally, the only limitation on suitable containers is that they be made from materials that are translucent to the radiant energy being employed.

In another aspect, generally, the invention features a contaminant detection system that includes a radiant energy source for directing radiant energy through a moving container, a detector for detecting a level of radiant energy scattered by contents of the moving container, and a processor for indicating the presence of a contaminant when the detected level of scattered radiant energy differs from a threshold level. The radiant energy source generally produces a frequency modulated laser beam, and scattered radiant energy detected by the detector is demodulated by the processor. The detector can include a turbid contaminant detector positioned near the bottom of the moving container for detecting light scattered by turbid liquid within the container, a foam detector positioned to detect light scattered by foam within the container, or both. Typically, the foam detector includes a vertical line array of optical fibers.

The system may also include an illuminator for directing radiant energy having a wide range of frequencies at the moving container so that the radiant energy is modified by contents of the moving container to produce modified radiant energy and a second detector for detecting a portion of the modified radiant energy so that the processor can obtain spectral information related to the contents of the container. The processor uses the spectral information to modify the threshold levels used for turbid contaminant and/or foam detection, and/or compares it with a library of reference spectra and indicates the presence or absence of a contaminant based on the relationship between the spectral information and the reference spectra. This system, which is preferably entirely automated, works effectively even when containers are moving past the system at rates on the order of 400 containers per minute or greater.

To ensure that spectral information is obtained from the detector at proper times, the system can include first, second and third position sensors that signal the processor when a container is in, respectively, a first, second or third position. The processor responds to the signal from the first position sensor by obtaining first position spectral information from the detector, to the signal from the second position sensor by obtaining second position spectral information from the detector, and to the signal from the third position sensor by measuring scattered radiant energy. The processor then compares the first and second position spectral information against the library of reference spectra, and compares the scattered energy information from measurements at the third position against a threshold, to determine whether a contaminant is present.

The contaminant detection system preferably is positioned downstream of a liquid supplier that adds a quantity of liquid to the container before the container arrives at the illuminator. To minimize the amount of liquid required, the illuminator, radiant energy source, and detectors are positioned so that radiant energy from the illuminator and the radiant energy source reaches the detectors after passing through and interacting with a region substantially near the bottom of the container. Typically this region is within one inch, and often within one quarter of an inch, of the bottom of the container.

Other features and advantages of the invention will be apparent from the following description of preferred embodiments, and from the claims.

DESCRIPTION OF PREFERRED EMBODIMENTS

Figure 1:
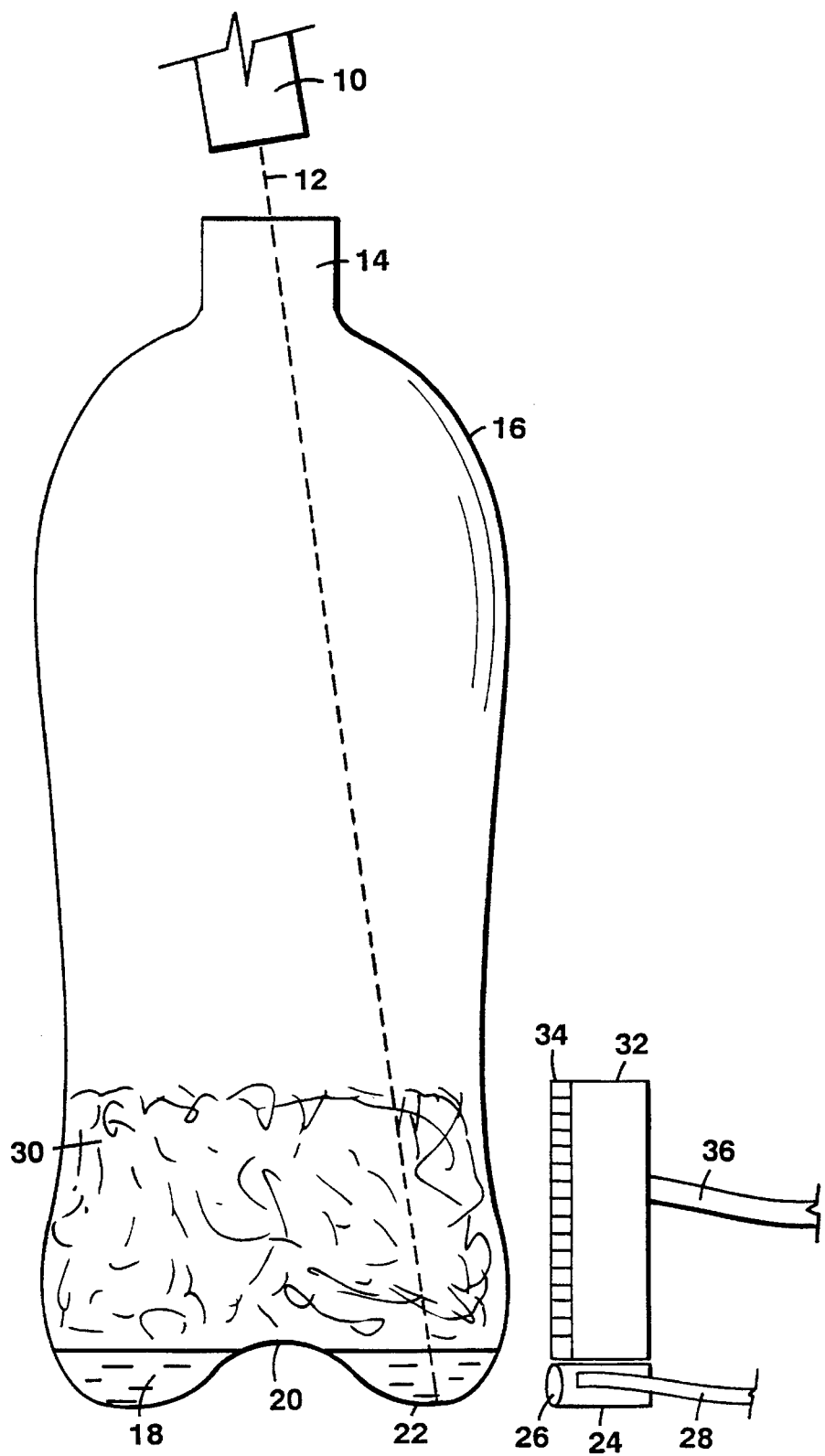
FIG. 1 is a side view of a bottle and a portion of a turbid contaminant and foam detection system.

With reference to FIG. 1, a laser source 10, such as a diode laser, is positioned to direct a laser beam 12 into the open neck 14 of a bottle 16 and into an annular ring of liquid 18 that is formed by a convex bulge 20 in the center of the base 22 of the bottle. When the liquid is turbid (e.g., due to the presence of a turbid contaminant), light scattered by particles in the liquid causes the laser beam to appear visually as a column of light in the liquid. A turbid contaminant detector 24 detects this column of light by monitoring the radiant energy scattered by the liquid. The turbid contaminant detector is positioned adjacent to the outer wall of the bottle near its base, and includes a collimating lens 26, an optical fiber 28 and a photodetector 29 (see FIG. 2), such as a silicon photodiode. The collimating lens 26 focusses any received radiant energy on the optical fiber 28. To reduce the effects of background radiation, the laser source 10 is configured to produce a frequency modulated laser beam 12, and the photodetector 29 is configured to detect only frequency modulated energy. Typically, the laser source 10 is a 670 nanometer diode laser modulated at 12 kHz.

When foam 30, such as would be caused by detergents and similar substances, is present on top of the liquid in the bottle, light scattered by the foam is detected by a foam detector 32 that includes optical fibers arranged in a vertical line array 34 adjacent to the bottle and in a round array 36 at the opposite end of the fibers. The foam detector is positioned next to the bottle with the vertical line array of fibers extending from about one quarter to two inches from the bottom of the bottle. The round array end of the fibers is positioned adjacent to a photodetector 38 (see FIG. 2) so that radiant energy transmitted by the fibers is incident on the photodetector 38. Thus, when foam is present, light scattered by the foam strikes one or more fibers of the vertical line array 34, and is directed to the photodetector 38. When radiant energy incident on photodetector 38 exceeds a threshold amount, this indicates that foam is present. Like photodetector 29, photodetector 38 is configured to detect only the frequency modulated energy produced by laser source 10.

Figure 2:
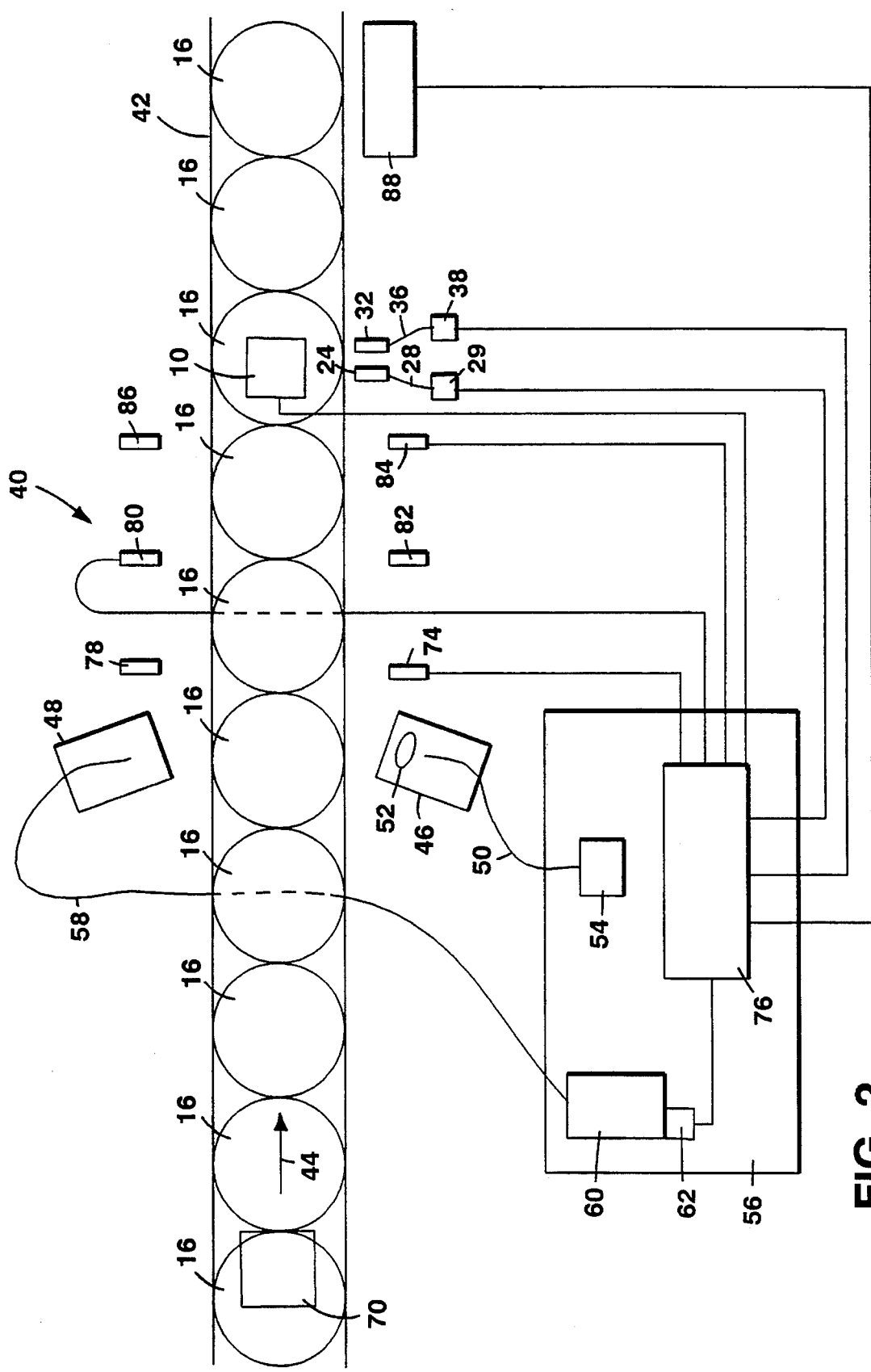
FIG. 2 is a schematic plan view of a portion of a bottle conveyor with a contaminant detection system including the turbid contaminant and foam detection system of FIG. 1.

As shown in FIG. 2, the laser source 10 and both photodetectors 29 and 38 are connected to a processor 76 that receives and electronically processes signals from the photodetectors 29 and 38 and other sensors, and controls the laser source 10 and other components, as part of a control unit 56.

With further reference to FIG. 2, turbid contaminant detector 24 and foam detector 32 are typically employed in conjunction with a spectral contaminant detection system 40 that is positioned to detect contaminants in containers, such as bottles 16, by analyzing spectral characteristics of liquids contained in the bottles as the bottles move along a conveyor 42 in the direction indicated by arrow 44. Because contaminants may be present as liquids in the bottles or may leach or desorb from walls of the bottles into liquids contained therein, the spectral characteristics of the liquids indicate the presence of such contaminants. Thus, by comparing the spectral characteristics of a bottle and the liquid contained therein to characteristics of bottles containing contaminated or uncontaminated liquids, the spectral contaminant detection system determines whether contaminants are present in the bottle.

As used herein, "contaminant" means any substance that can be detected in a container by the detection system of the invention and whose presence is incompatible with the product with which the container is to be filled. For example, detergents are contaminants with respect to beverage containers, and flavored beverages may be contaminants with respect to bottled water.

System 40 includes a radiant energy source or illuminator 46 and a detector 48. The illuminator is positioned to direct radiant energy at a bottle so that the radiant energy encounters liquid contained in the bottle. The detector is positioned to detect radiant energy from the illuminator after that radiant energy has encountered the liquid contained in the bottle.

The illuminator includes a fiber optic bundle 50 coupled to a lens 52. The fiber optic bundle transmits radiant energy from a lamp 54 located in a control unit 56 to the lens 52, which focusses the radiant energy and directs the focussed radiant energy toward a bottle 16. The lamp is typically a halogen lamp, but other sources of radiant energy such as, for example, a xenon flashtube that is controlled to strobe at appropriate times, could be used.

The detector 48 includes a fiber optic bundle 58 that receives some of the radiant energy from lens 52 after it has encountered liquid in the bottle. Fiber optic bundle 58 transmits the radiant energy to an optical spectrometer 60 in the control unit 56. Within the optical spectrometer, a series of mirrors focusses the transmitted radiant energy on a diffraction grating that separates the transmitted radiant energy into wavelength components and directs each wavelength component to a different pixel of a linear detection array 62. Typically, linear detection array 62 is implemented as a diode array or a charge coupled device ("CCD") having about one thousand pixels.

Use of fiber optic bundles 50 and 58, which may be two meters or greater in length, allows the control unit 56 to be positioned a substantial distance away from the conveyor and the bottles, and thereby minimizes the exposure of the control unit to the potentially wet or otherwise hostile environment at the conveyor.

Figure 4:
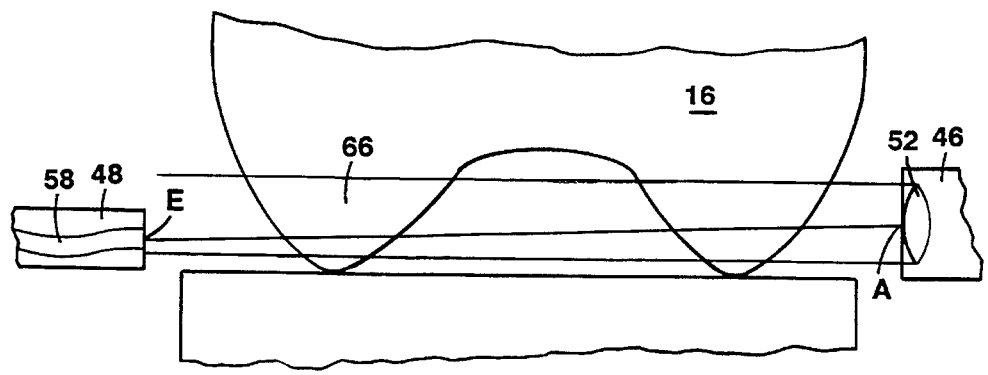
FIGS. 3 and 4 are side views of a portion of a bottle and some of the sensors of the system of FIG. 2.
Figure 3:
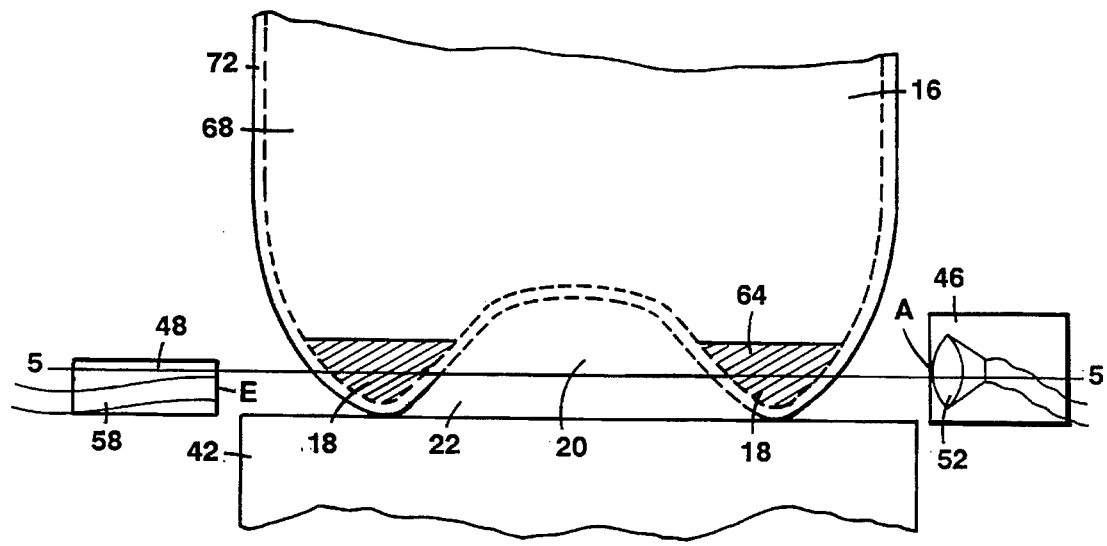

With reference to FIGS. 3 and 4, illuminator 46 and detector 48 are positioned so that the radiant energy from lens 52 is directed at a region 64 near the bottom of each bottle 16, with the lens being centered about one half inch above the bottom of the bottle, and fiber 58 being centered about one quarter inch above the bottom of the bottle. The illuminator and the detector are aimed such that their axes of emission and reception are not aligned (i.e., the illuminator and the detector, respectively, emit and receive radiation in directions that are not parallel to each other) and are not normal to the direction of movement of the bottles. This positioning requires the presence of only minimal amounts of liquid 18 in the bottle. In the preferred embodiment, each bottle needs to contain as little as about four and one half milliliters of liquid. In addition to being positioned near the bottom of the bottle, the illuminator and the detector are positioned close to the conveyor 42, typically within one eighth of an inch. As best illustrated in FIG. 4, a beam of light 66 from the illuminator is directed at and above the horizontal plane occupied by the detector. As also illustrated in FIG. 4, the mean light path from the lens of the illuminator to the fiber 58 of the detector is along path AE.

Although bottles and containers of various shapes may be inspected by system 40, the bottle 16 shown in FIGS. 1 and 3–6 has a base 22 with a convex bulge 20 in its bottom that causes liquid 18 near the bottom to form a concentric annular ring around the bulge. Because the base has a smaller diameter than a main portion 68 of the bottle, and because the illuminator and the detector are positioned near the bottom of the bottle, bottles can be moved along conveyor 42 with no spacing—i.e., in contact with other bottles, with no interference by a bottle with measurement taken by system 40 on an adjacent bottle.

A liquid supplier 70, positioned upstream of illuminator 46 and laser source 10, adds a sufficient amount of liquid 18 to each bottle to ensure that radiation emitted from the illuminator, and from the laser source, will encounter liquid in the bottom of each bottle. Generally, because extra liquid does not affect the performance of system 40, the liquid supplier adds liquid to each bottle without regard to whether a bottle already contains liquid. Addition of liquid by the supplier 70, which may be an injector timed to inject pulses of liquid into the open top of each bottle as the bottle passes underneath the supplier, may assist in leaching contaminants from the bottle walls as well as ensuring the presence of a sufficient amount of liquid for detection. Typically, the liquid supplier delivers the liquid at high pressure, which agitates any particles resulting from turbid contaminants within the bottle and causes foam 30 to be produced if a foaming contaminant is present. When the liquid supplier delivers the liquid in multiple bursts, the first burst washes down contaminants from the wall 72 of the bottle and subsequent bursts agitate those contaminants. Typically, the liquid supplied by the liquid supplier is water or a dilute aqueous solution. However, in some applications, other liquids could be used. For example, a liquid that changes color in the presence of an otherwise difficult to detect contaminant could be used to ease detection of that contaminant.

Figure 5:
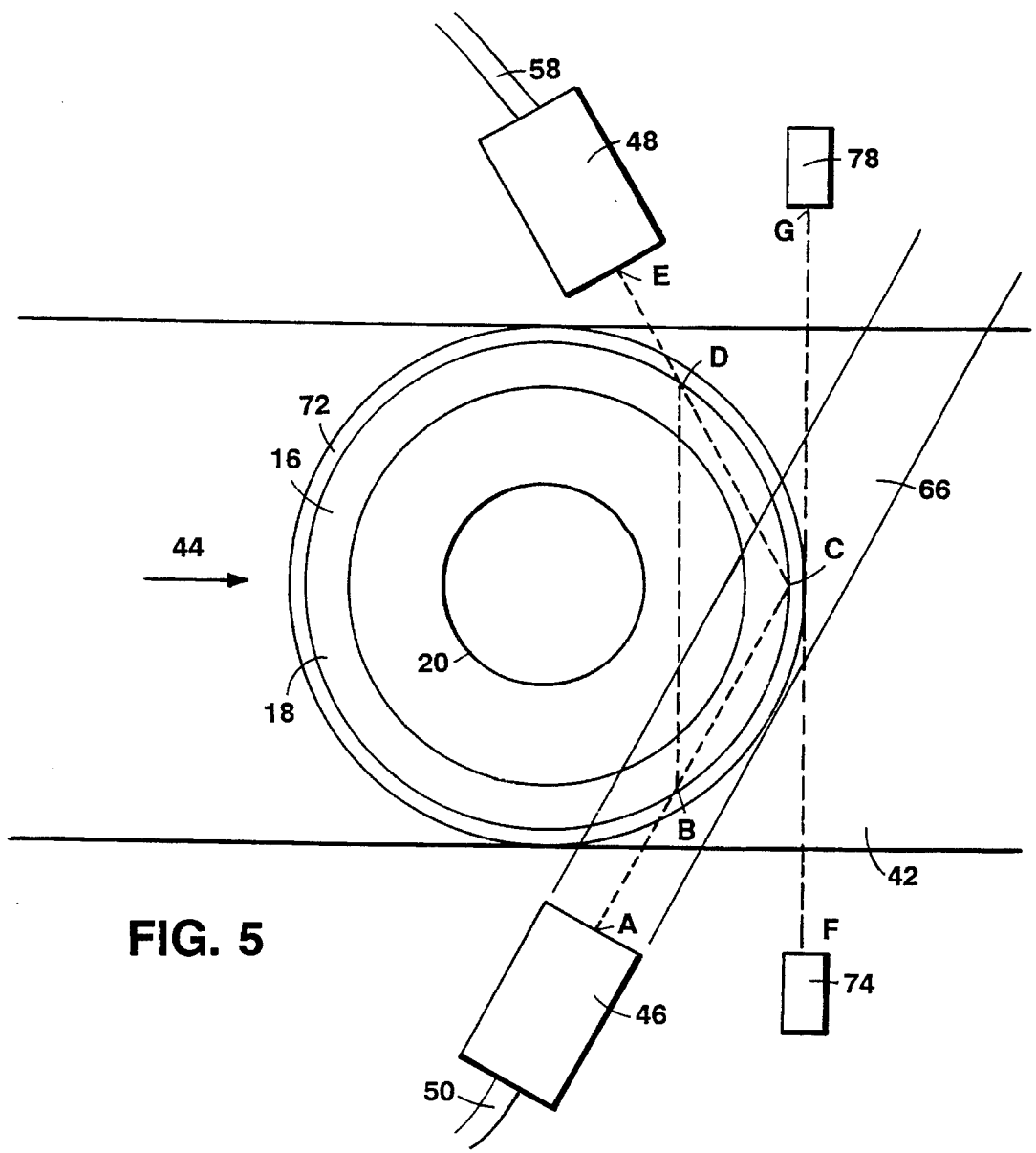
FIG. 5 is a cutaway top view taken along line 5—5 of FIG. 3 of a bottle and sensors of the system of FIG. 2 with the bottle in a first detection position.

With reference to FIG. 5, in which, for simplicity, only a single bottle 16 is shown, in operation of spectral contaminant detection system 40, a first position sensor 74 signals a processor 76 in control unit 56 when the bottle is positioned suitably to produce a first spectrum for liquid 18 and any contaminants contained therein. The first position sensor signals the processor when the bottle is positioned so that a portion of the radiant energy that reaches the detector 48 from the illuminator 46 travels along a path ABC, reflects from the inside surface of a wall 72 of the bottle, and continues along a path CDE to the detector. Because this position maximizes the length of the path that radiant energy takes through the liquid, and thereby maximizes the absorption of radiant energy by the liquid and any contaminants contained therein, the measured spectrum is referred to as an absorption spectrum. Typically, the illuminator and the detector are positioned so that the angle ACE is within a range from 100°–140° with about 120° being most typical.

In actual operation, the portion of the radiant energy produced by the illuminator that actually reaches the detector travels by multiple paths that are significantly more complicated than the path described above. For example, the actual path is affected by reflection from the wall of the bottle and the interface between the liquid and air in the bottle. In addition, due to the presence of the liquid, the radiant energy is refracted at points B and D, so that some of it travels approximately along a path BD before reaching the detector. The radiant energy is affected also by scattering at the wall of the bottle and at the convex bulge 20, and can travel along complicated paths that include several internal reflections within the bottle.

The first position sensor 74 signals the processor 76 when the leading edge of a bottle 16 crosses a line FG between the first position sensor 74 and a first light source 78. When the bottle crosses line FG, the bottle interrupts or otherwise causes a change in the level of light (radiation) from the first light source that reaches the first position sensor. The first position sensor generates the signal to the processor 76 in response to this change in the level of light.

Upon receiving the signal from the first position sensor, the processor causes linear detection array 62 to record the spectrum produced by spectrometer 60 of the radiant energy detected by detector 48. The processor then sequentially reads the linear detection array 62 to generate a vector that represents the intensity of radiant energy received at each pixel of the linear detection array, and stores the vector as an absorption spectrum associated with the bottle being examined. The processor makes no determination as to the incident light produced by the illuminator. Typically, each pixel of the absorption spectrum is represented by twelve bits. In the preferred embodiment, the processor 76 is implemented using an Intel 486 processor running at sixty six megahertz.

Figure 6:
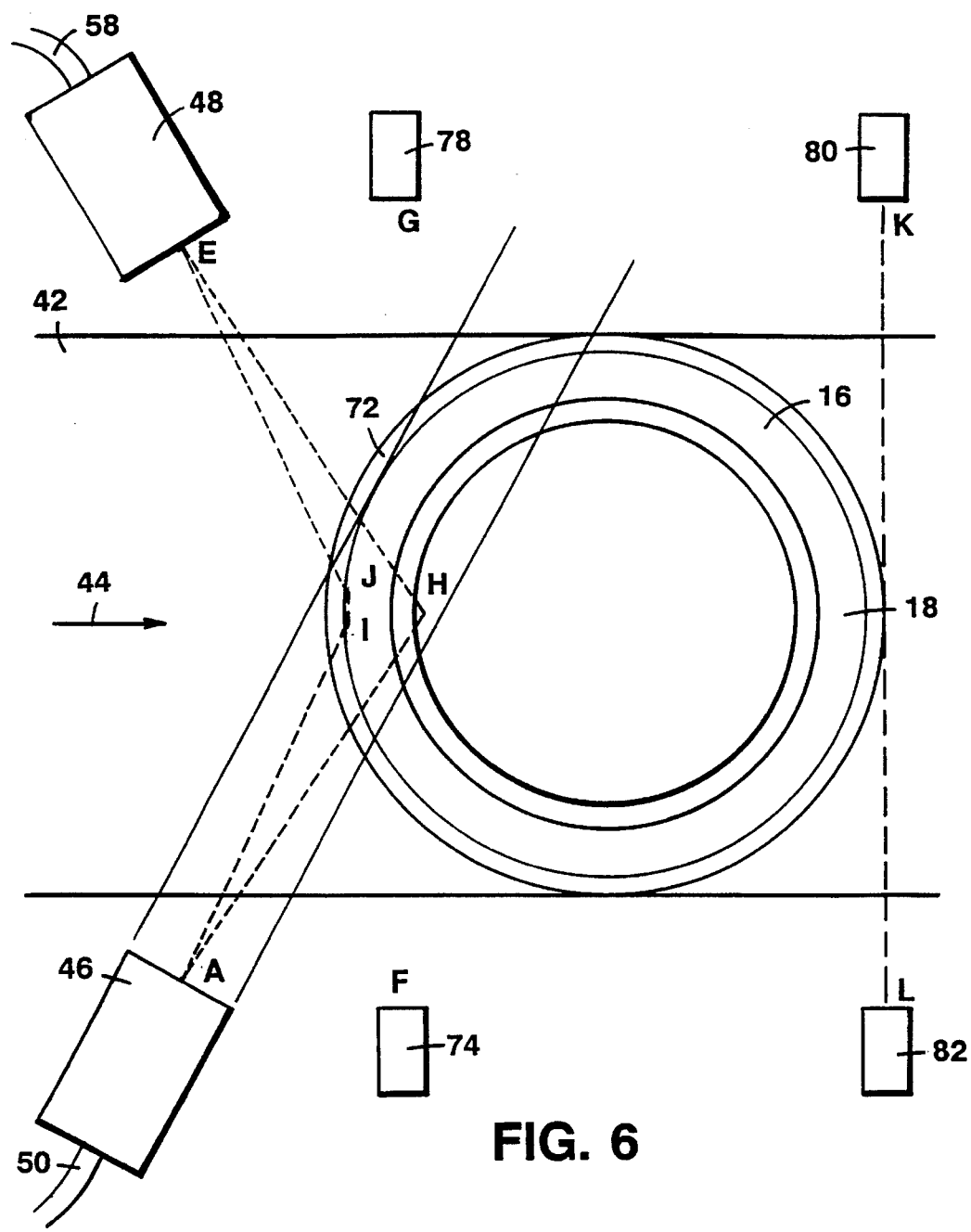
FIG. 6 is a similar view to that shown in FIG. 5, with the bottle in a second detection position.

With reference also to FIG. 6, a second position sensor 80 signals the processor when a bottle is positioned suitably to produce a second spectrum for liquid and any contaminants contained in the bottle. The second position sensor signals the processor when the bottle is positioned so that radiant energy that reaches the detector from the illuminator 46 travels approximately along a path AH, reflects from liquid 18 near the inner surface of wall 72, and continues approximately along a path HE to the detector 48. Because most of the radiant energy reaching the detector does so by reflection rather than transmission, the measured spectrum for this second position of the bottle is referred to herein as a reflection spectrum.

It should be understood that the path of the radiant energy for the measurement at a second position of the bottle is, like that of the first position, more complicated than illustrated in FIG. 6. For example, light could also travel along a path AI, refract at the interface between the wall 72 and the liquid, travel along a path IJ, refract at the interface between the liquid and the wall, and travel along path JE to the detector 48. Moreover, the intensity of the energy received by the detector for the second position is typically lower than that received for the first position since, when the bottle is in the second position, most of the energy is transmitted beyond point H.

The second position sensor 80 signals the processor 76 when a leading edge of a bottle crosses a line KL between the second position sensor and a second light source 82. The second position sensor and the second light source are typically located downstream of the first position sensor 74 and the first light source 78 by slightly less than the diameter of a bottle, and operate identically to the first position sensor and the first light source. To prevent cross talk caused by the first position sensor responding to light produced by the second light source, or by the second position sensor responding to light produced by the first light source, the sensors and light sources are positioned with the first position sensor and the second light source on one side of the conveyor 42, and the second position sensor and the first light source on the other side of the conveyor. In an alternative approach to preventing cross talk, the sensor/light source pairs are configured to respond to different frequencies of light.

Upon receiving the signal from the second position sensor, the processor 76 causes the linear detection array 62 to record the spectrum produced by the spectrometer 60 of the radiant energy detected by the detector 48. The processor then stores the recorded spectrum as a reflection spectrum associated with the bottle being examined.

Figure 7:
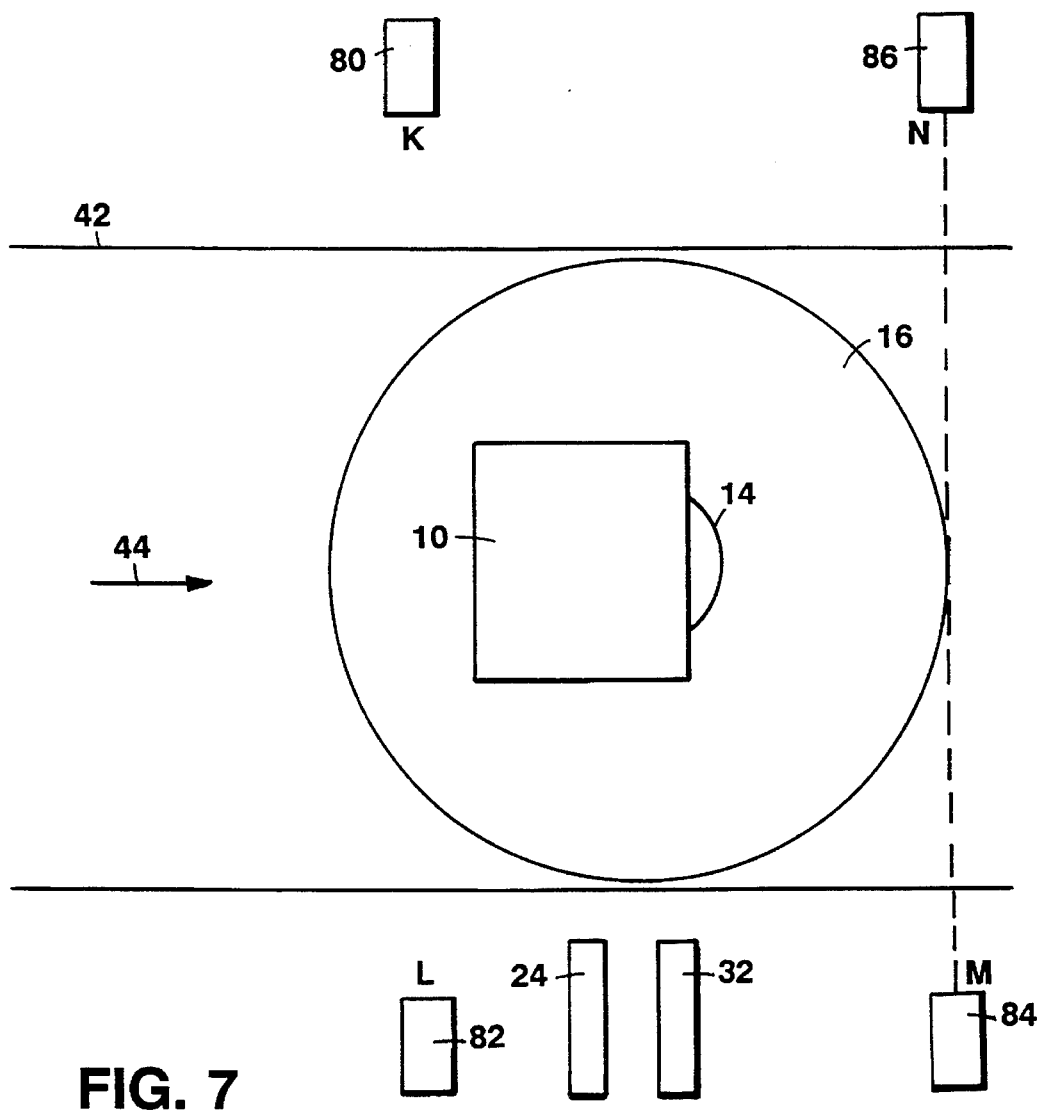
FIG. 7 is a top view of a bottle and sensors of the system of FIG. 2 with the bottle in a third detection position.

With reference also to FIG. 7, a third position sensor 84 signals the processor 76 when a bottle is positioned suitably to produce a turbidity/foam measurement for liquid and any contaminants contained in the bottle. The third position sensor signals the processor when the bottle is positioned so that scattered light from laser source 10 is directed at the turbid contaminant detector 24 and the foam detector 32, which occurs when a leading edge of a bottle crosses a line MN between the third position sensor 84 and a third light source 86. The third position sensor and the third light source are typically located downstream of the second position sensor 80 and the second light source 82, and operate identically to the second position sensor and the second light source. To prevent cross talk caused by the second position sensor responding to light produced by the third light source, or by the third position sensor responding to light produced by the second light source, the sensors and light sources are positioned with the second position sensor and the third light source on one side of the conveyor 42, and the third position sensor and the second light source on the other side of the conveyor. In an alternative approach to preventing cross talk, the sensor/light source pairs are configured to respond to different frequencies of light.

The signals from photodetectors 29 and 38 are continually amplified, demodulated, and converted to digital values by the processor 76. Upon receiving the signal from the third position sensor, the processor latches the digital values to record the level of modulated energy detected by photodetector 29 and photodetector 38. The processor then stores the recorded turbidity and foam energy levels for the bottle being examined.

The processor 76 utilizes spectra to determine whether a bottle 16 contains contaminants by comparing the absorption and reflection spectra associated with the bottle to a library of reference spectra associated with bottles containing acceptable substances. For example, for bottles to be filled with a beverage, acceptable substances would include water, beverage residue, and the aqueous solution supplied by liquid supplier 70. The processor compares the spectra by computing either the Pearson's correlation or the Spearman's correlation for the vectors representing each spectrum.

Pearson's correlation, which is described, for example, in Pfaffenberger & Patterson, *Statistical Methods For Business and Economics*, p. 429 (1977, Richard D. Irwin, Inc., Homewood, Ill.), determines whether two vectors are related by a linear mapping, and is determined as:

$$r = \frac{\sum_{i=1}^{n} (x_i y_i)}{\sqrt{\sum_{i=1}^{n} (x_i)^2} \sqrt{\sum_{i=1}^{n} (y_i)^2}}$$

where $x_i$ equals the ith component of the vector X minus the average value of the components of the vector X, $y_i$ equals the ith component of the vector Y minus the average value of the components of the vector Y, and n equals the number of components in vector X or vector Y.

Spearman's correlation, which is described in Pfaffenberger & Patterson at p. 679, arranges the elements of each vector in rank order and determines whether two vectors have similar rank orders, and is determined as:

$$\rho = 1 - 6 \sum_{i=1}^{n} \frac{[R(X_i) - R(Y_i)]^2}{n(n^2 - 1)}$$

where $R(X_i)$ equals the rank of the ith component of the vector X relative to the other components of the vector X, $R(Y_i)$ equals the rank of the ith component of the vector Y relative to the other components of the vector Y, and each tied rank is assigned the average of the ranks that would have been assigned had there been no ties (e.g., if the fifth and sixth ranked components have equal values, they are each assigned a rank of 5.5).

If the spectra associated with the bottle correlate within a predefined threshold—e.g., by greater than 90%—to a pair of reference spectra representing acceptable bottle content, the processor allows the bottle to continue along the conveyor for filling or other testing. If not, the processor sends a signal to a suitable rejector 88, and the rejector responds by removing the bottle from the conveyor.

The processor also sends a signal to the rejector if the turbidity or foam energy levels exceed thresholds which indicate that a turbid or foaming contaminant is present in the bottle. These thresholds are typically varied based on the color spectra of the liquid in the bottle. For example, some carbonated beverages contain fruit juice and are slightly turbid. If the color spectra of the liquid matches reference spectra associated with such a beverage, the turbidity threshold is increased. Similarly, if the color spectra of the liquid matches reference spectra associated with water, the turbidity and foaming thresholds are decreased.

An advantage of comparing the spectra associated with a bottle to reference spectra associated with bottles containing acceptable materials, rather than comparing with spectra associated with bottles containing unacceptable contaminants, is that the former imposes less computational burden on the processor. Moreover, detection accuracy of the system may be higher due to a reduced likelihood of failing to detect contaminants.

The computational burden is reduced because the number of acceptable reference spectra is typically quite limited, while, considering the number of potential contaminants and the various ways in which the contaminants can be combined, the number of unacceptable reference spectra may be virtually unlimited. For example, to detect contaminants in refillable polyethylene terephthalate cola bottles, it has been found that a library consisting of ten reference spectra—the absorption and reflection spectra associated with two liquid levels of water and three liquid levels of cola—is adequate.

The detection accuracy of the system is higher because, unlike a system in which only bottles having spectra similar to reference spectra associated with known contaminants are rejected, the system is able to reject a bottle that contains a previously unknown contaminant or a previously unknown combination of known contaminants.

Though comparison to acceptable reference spectra offers considerable advantages, the spectral contaminant detection system could be configured to compare the spectra associated with unacceptable spectra or a combination of acceptable and unacceptable spectra. For example, to screen out, for testing or other purposes, only bottles containing particular contaminants such as a blue fabric softener or a green disinfectant, the spectra associated with the bottles could be compared to reference spectra associated with the particular contaminants. Similarly, if the spectra associated with a bottle containing a particular contaminant were close to the spectra of an uncontaminated bottle, it would be useful to accept the bottle only when its spectra are sufficiently similar to the spectra of the uncontaminated bottle and sufficiently different from the spectra of the contaminated bottle.

Typically, the processor 76 combines the detection approaches as follows. If the turbid or foaming energy levels indicate the presence of turbid or foaming contaminants, the processor signals the rejector 88 to reject the bottle unless the spectral information indicates that the liquid is an acceptable turbid or foaming liquid. The processor also signals the rejector if the spectral information confirms that the liquid is unacceptable, or fails to confirm that the liquid is acceptable.

The lamp 54 of the illuminator 46 may be a wideband source that produces radiant energy in a wavelength range from about 250 nanometers to about 2000 nanometers, which corresponds to visible light and infrared energy. The linear detection array 62 produces spectra for the wavelength range from 320 to 1200 nanometers, which corresponds primarily to visible light. Within this range, for correlation purposes, the range from about 485 to about 600 nanometers has been found to be most useful for absorption spectra, and the range from about 350 to about 750 nanometers has been found to be most useful for reflection spectra. In another approach, infrared wavelengths could be emphasized. This would be useful, for example, in detecting the presence of sugars in bottles to be filled with water because sugar absorbs radiation of wavelengths between 1300 and 1600 nanometers. Indeed, because infrared spectra can be used to identify almost all organic compounds, a system emphasizing the infrared spectra could be used as a general chemical detector.

The invention may be in the form of other embodiments. For example, though conveyor 42 is illustrated as a straight conveyor, the system could be applied effectively to a system in which the bottles are held in the periphery of a rotating wheel as they pass by the illuminator 46 and the detector 48. In this case, though bottles would travel in an arc as they moved from the first position to the second position, their spectra would still be determined as illustrated in FIGS. 5 and 6. In another variation, the contaminant detection system may generate and utilize only a single spectrum, such as an absorption spectrum or a reflection spectrum, for each bottle. Limited tests with a system utilizing an absorption spectrum alone or a reflection spectrum alone have generally shown lower overall accuracy in detection of contaminants, and have tended to produce more false positives, than a system generating and using both absorption and reflection spectra. However, a single spectrum may be adequate in certain applications. For example, an absorption spectrum may be sufficient for detection of contaminants in liquid/contaminant mixtures of high transmissivity.

Also, instead of varying the position of the bottle relative to the illuminator and the detector to obtain different spectral characteristics, two or more sets of illuminators and detectors, having similar or different characteristics, and being operable simultaneously or sequentially, could be employed. For example, a first illuminator and detector pair could be configured and oriented to obtain a visible absorption spectrum while a second illuminator and detector pair was configured to obtain an infrared reflection spectrum.

In addition, detection of turbid contaminant could be combined with spectral detection. In this approach, the laser source 10 would be positioned so that light scattered by turbid contaminants would strike the detector 48. The processor would then determine that a turbid contaminant was present whenever the spectrum of the liquid took on an excessive value at the frequency produced by the laser source.

Also, transmitted light could be measured rather than scattered light in the detection of turbid contaminants. In this approach, the turbid contaminant detector would be placed under the bottle, and the presence of a turbid contaminant would be signalled when the level of energy received by the detector is less than a particular threshold.

Finally, in yet another approach, turbid contaminants could be detected by monitoring the resolvability of an image, since turbidity causes a loss of spatial coherence. For example, a bar pattern could be placed on the conveyor and a bar reader would be positioned to read the bar pattern through the liquid contained in the bottle. The bar reader would then signal the presence of a turbid contaminant upon detection of flickering in the bar pattern.

What is claimed is:

1. A method of detecting a contaminant in a moving container, comprising:

directing radiant energy into an open top of the moving container, electronically detecting a level of radiant energy scattered through a side of the moving container near a bottom of the moving container by contents of the moving container, and indicating the presence of a contaminant when the detected level of scattered radiant energy differs from a threshold level.

2. The method of claim 1, wherein said detecting step comprises detecting a level of radiant energy scattered by turbid liquid within the moving container.

3. The method of claim 2, wherein said detecting step further comprises detecting a level of radiant energy scattered by foam within the moving container.

4. The method of claim 1, wherein said directing step comprises directing radiant energy toward the bottom of the moving container, said detecting step comprises measuring a level of radiant energy scattered through the side of the moving container by contents of the moving container, and said indicating step comprises indicating the presence of a contaminant when the measured level of radiant energy exceeds a threshold level.

5. The method of claim 1 including modulating the radiant energy before directing it into the moving container, and demodulating the radiant energy when detecting the scattered radiant energy.

6. The method of claim 1 including:
   directing wideband radiant energy at the moving container so that the wideband radiant energy is modified by contents of the moving container to produce modified wideband radiant energy,
   detecting a portion of the modified wideband radiant energy,
   obtaining spectral information from the detected portion of modified wideband radiant energy,
   modifying the threshold level based on the obtained spectral information.

7. The method of claim 6 including:
   storing reference spectral information related to at least one container having known contents, and
   comparing the spectral information obtained from the detected portion of modified wideband radiant energy with the reference spectral information using correlation techniques, and wherein said indicating step further comprises indicating the presence of a contaminant based on the relationship between the spectral information obtained from the detected portion of modified wideband radiant energy and the reference spectral information.

8. The method of claim 7 including:
   detecting first and second portions of wideband radiant energy modified by contents of the moving container,
   obtaining first and second sets of spectral information, respectively, from the first and second detected portions of modified wideband radiant energy without measuring the intensity of the wideband radiant energy directed at the moving container,
   comparing the first and second sets of spectral information with the reference spectral information using correlation techniques, and
   indicating the presence of a contaminant based on the relationship between the first and second sets of spectral information and the reference spectral information.

9. The method of claim 8, wherein the moving container is located substantially in a first position when the first portion of wideband radiant energy is detected, is located substantially in a second position when the second portion of wideband radiant energy is detected, and is located substantially in a third position when the level of radiant energy is detected, said method further comprising the step of moving the moving container from the first position to the second position, and thereafter from the second position to the third position.

10. The method of claim 7, further comprising the step of adding a quantity of liquid to the moving container prior to said directing step, and wherein said directing step includes directing radiant energy at the moving container near the bottom thereof.

11. The method of claim 10, wherein said adding step comprises adding liquid at high pressures to agitate the contents of the moving container.

12. The method of claim 10, wherein said adding step comprises adding liquid in multiple bursts to agitate the contents of the moving container.

13. The method of claim 1, wherein the step of directing comprises directing radiant energy into an opening in the moving container.

14. A method of detecting a contaminant in a moving container, comprising:
   storing reference spectral information related to at least one container having known contents,
   directing modulated radiant energy having a narrow range of wavelengths into the moving container through an open top of the container,
   detecting a level of modulated radiant energy scattered through a side of the moving container near a bottom of the moving container by turbid liquid within the moving container,
   directing wideband radiant energy having a wide range of wavelengths at the moving container so that the wideband radiant energy is modified by contents of the moving container to produce modified wideband radiant energy,
   detecting a portion of the modified wideband radiant energy,
   obtaining spectral information from the detected portion of modified wideband radiant energy,
   comparing the spectral information obtained from the detected portion of modified wideband radiant energy with the reference spectral information using correlation techniques, and
   indicating the presence of a contaminant when the detected level of scattered modulated radiant energy differs from a threshold level or based on the relationship between the spectral information obtained from the detected portion of modified wideband radiant energy and the reference spectral information.

15. The method of claim 14 further comprising modifying the threshold level based on the obtained spectral information.

16. The method of claim 14 further comprising detecting a level of modulated radiant energy scattered by foam within the moving container, and wherein said indicating step includes indicating the presence of a contaminant when the detected level of modulated radiant energy scattered by foam differs from a threshold level.

17. A contaminant detection system comprising:
   a radiant energy source for directing radiant energy into a moving container, and configured to direct the radiant energy through an open top of the moving container,
   a detector for detecting a level of radiant energy scattered through a side of the moving container near a bottom of the moving container by contents of the moving container, and
   a processor for indicating the presence of a contaminant when the detected level of scattered radiant energy differs from a threshold level.

18. The system of claim 17, wherein said detector comprises a turbid contaminant detector positioned near the bottom of the moving container for detecting light scattered by turbid liquid within the container.

19. The system of claim 18, further comprising a foam detector positioned to detect light scattered by foam within the container.

20. The system of claim 19, wherein the foam detector comprises a vertical line array of optical fibers.

21. The system of claim 17, wherein said detector comprises a foam detector positioned to detect light scattered by foam within the container.

22. The system of claim 21, wherein the foam detector comprises a vertical line array of optical fibers.

23. The system of claim 17, wherein the radiant energy source is a laser source.

24. The system of claim 17, wherein said detector is a first detector, and further comprising:

an illuminator for directing wideband radiant energy at the moving container so that the wideband radiant energy is modified by contents of the moving container to produce modified wideband radiant energy, and a second detector for detecting a portion of the modified wideband radiant energy, wherein the processor is operable to obtain spectral information from the detected portion of modified wideband radiant energy.

25. The system of claim 24 wherein the processor is operable to modify the threshold level based on the obtained spectral information.

26. The system of claim 24, wherein said processor is an electronic computer operable to process information from at least 400 containers per minute.

27. For use with a container inspection system having a conveyor for moving containers and a liquid supplier for adding uncontaminated liquid to each container, a contaminant detector to be mounted near said conveyor at a location downstream of the liquid supplier, said contaminant detector comprising:

a radiant energy source for directing radiant energy into an open top of a moving container, a first detector for detecting a level of radiant energy scattered by contents of the moving container through a side of the moving container near a bottom of the moving container, and a processor for indicating the presence of a contaminant when the detected level of scattered radiant energy differs from a threshold level.

\* \* \* \* \*